(12) United States Patent
Walter et al.

(10) Patent No.: US 8,268,877 B2
(45) Date of Patent: Sep. 18, 2012

(54) MICROBIOCIDES

(75) Inventors: Harald Walter, Stein (CH); Daniel Stierli, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/382,836

(22) PCT Filed: Jun. 7, 2010

(86) PCT No.: PCT/EP2010/057878
§ 371 (c)(1),
(2), (4) Date: Jan. 6, 2012

(87) PCT Pub. No.: WO2011/003683
PCT Pub. Date: Jan. 13, 2011

(65) Prior Publication Data
US 2012/0108645 A1    May 3, 2012

(30) Foreign Application Priority Data
Jul. 7, 2009   (EP) ..................................... 09164788

(51) Int. Cl.
*A61K 31/4155*   (2006.01)
*C07D 231/10*   (2006.01)

(52) U.S. Cl. ..................................... 514/406; 548/364.4
(58) Field of Classification Search .................. 514/406; 548/364.4
See application file for complete search history.

(56) References Cited

FOREIGN PATENT DOCUMENTS
WO    2009/003672    1/2009

*Primary Examiner* — Joseph K. McKane
*Assistant Examiner* — Samantha Shterengarts
(74) *Attorney, Agent, or Firm* — Kody Jones

(57) ABSTRACT

Compounds of formula (I) in which the substituents are as defined in claim 1, are suitable for use as microbiocides.

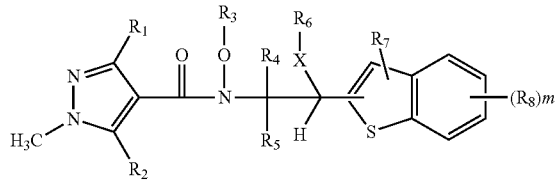

6 Claims, No Drawings

MICROBIOCIDES

This application is a 371 of International Application No. PCT/EP2010/057878 filed Jun. 7, 2010, which claims priority to EP 09164788.3 filed Jul. 7, 2009, the contents of which are incorporated herein by reference.

The present invention relates to novel microbiocidally active, in particular fungicidally active, benzthienyl ethyl amides. It further relates to intermediates used in the preparation of these compounds, to compositions which comprise these compounds and to their use in agriculture or horticulture for controlling or preventing infestation of plants by phytopathogenic microorganisms, preferably fungi.

Benzthienyl ethyl amides and their use as fungicides are described for example in WO 2009/003672. It has been found that novel thienyl ethyl amides with a specific substitution pattern have microbiocidal activity.

The present invention accordingly relates to N-alkoxycarboxamides of formula I

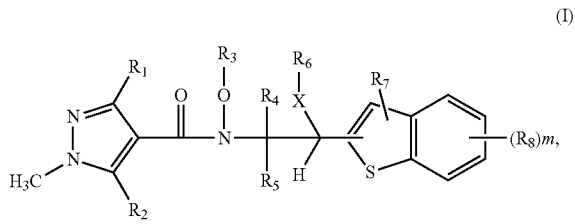

wherein
$R_1$ is $C_1$-$C_4$alkyl or $C_1$-$C_4$haloalkyl;
$R_2$ is hydrogen, fluoro or chloro;
$R_3$ is hydrogen or $C_1$-$C_4$alkyl;
$R_4$ and $R_5$, independently from each other, are hydrogen or $C_1$-$C_4$alkyl;
X is oxygen, sulfur or absent;
$R_6$ is $C_1$-$C_4$alkyl or $C_1$-$C_4$haloalkyl if X is oxygen or sulfur, or is hydrogen if X is absent;
$R_7$ and $R_8$ independently from each other, are hydrogen or halogen; with the proviso that at least one of $R_7$ and $R_8$ is different from hydrogen;
m is 1, 2, 3, or 4;
and agrochemically acceptable salts/isomers/structural isomers/stereoisomers/diastereoisomers/enantio-mers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy and alkynyl radicals are derived from the alkyl radicals mentioned. Halogen is generally fluorine, chlorine, bromine or iodine, preferably fluorine, bromine or chlorine. This also applies, correspondingly, to halogen in combination with other meanings, such as halogenalkyl. Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy.

In a preferred group of compounds of formula I, $R_1$ is difluoromethyl, trifluoromethyl or methyl; $R_2$ is hydrogen or fluoro; $R_3$ is hydrogen, methyl or ethyl; $R_4$ is hydrogen or methyl; $R_5$ is hydrogen or methyl; $R_6$ is methyl; X is oxygen; $R_7$, and $R_8$ independently of each other, are hydrogen, chloro or bromo; with the proviso that at least one of $R_7$ and $R_8$ is different from hydrogen.

In a preferred group of compounds of formula I, $R_1$ is difluoromethyl, trifluoromethyl or methyl; $R_2$ is hydrogen or fluoro; $R_3$ is hydrogen, methyl or ethyl; $R_4$ is hydrogen or methyl; $R_5$ is hydrogen or methyl; $R_6$ is methyl; X is oxygen; m is 1 or 2, $R_7$, and $R_8$ independently of each other, are hydrogen, chloro or bromo; with the proviso that at least one of $R_7$ and $R_8$ is different from hydrogen.

In said preferred 2 groups above, further compounds of formula I are of particular relevance wherein X is absent and $R_6$ is hydrogen.

In said preferred 2 groups above, further compounds of formula I are of particular relevance wherein X is oxygen and $R_6$ is methyl.

In said preferred 2 groups, m is preferably 1.

In preferred compounds of formula I, independently from each other,
a) $R_1$ is difluoromethyl, trifluoromethyl or methyl,
b) $R_2$ is hydrogen or fluoro;
d) $R_3$ is hydrogen, methyl or ethyl;
e) $R_4$ is hydrogen or methyl;
f) $R_5$ is hydrogen or methyl;
g) $R_6$ is methyl;
h) X is oxygen;
i) X is absent and $R_6$ is hydrogen;
j) $R_7$, and $R_8$ independently of each other, are hydrogen, chloro or bromo; with the proviso that at least one of $R_7$ and $R_8$ is different from hydrogen.

Especially preferred compounds of formula I are those, wherein
$R_1$ is difluoromethyl or trifluoromethyl;
$R_2$ is hydrogen;
$R_3$ is methyl;
$R_4$ is hydrogen;
$R_5$ is methyl;
X is absent and $R_6$ is hydrogen; or
X is oxygen and $R_6$ is methyl;
$R_7$ and $R_8$ independently of each other, are hydrogen or chloro; with the proviso that at least one of $R_7$ and $R_8$ is different from hydrogen.

Especially preferred compounds of formula I are those, wherein
$R_1$ is difluoromethyl or trifluoromethyl;
$R_2$ is hydrogen;
$R_3$ is methyl;
$R_4$ is hydrogen;
$R_5$ is methyl;
X is absent and $R_6$ is hydrogen; or
X is oxygen and $R_6$ is methyl;
m is 1;
$R_7$ and $R_8$ independently of each other, are hydrogen or chloro; with the proviso that at least one of $R_7$ and $R_8$ is different from hydrogen.

A further preferred group of compounds of formula I is represented by the compounds of formula Ia:

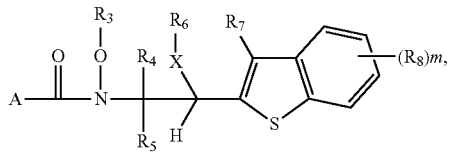
(Ia)

wherein A is selected from the groups consisting of $A_1$,

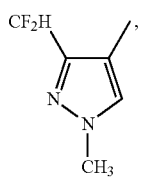
($A_1$)

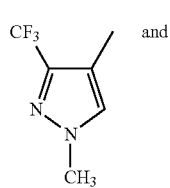
($A_2$)

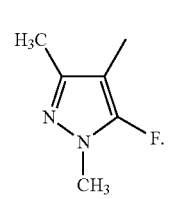
($A_3$)

and $R_3$, $R_4$, $R_6$, $R_7$, $R_8$, m and X are as defined under formula I above and $R_5$ is hydrogen.

A further preferred group of compounds of formula I is represented by the compounds of formula Ib:

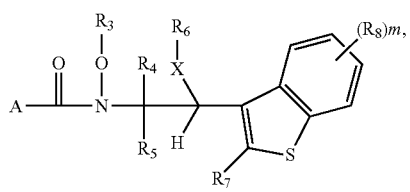
(Ib)

wherein A is selected from the groups consisting of $A_1$,

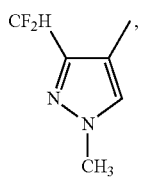
($A_1$)

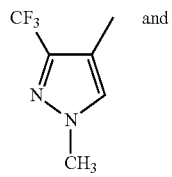
($A_2$)

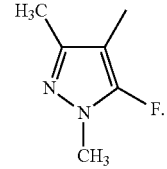
($A_3$)

and $R_3$, $R_4$, $R_6$, $R_7$, $R_8$, m and X are as defined under formula I above and $R_5$ is hydrogen.

In preferred compounds of formula Ia and Ib, independently from each other,
a) $R_3$ is hydrogen, methyl or ethyl;
b) $R_4$ is hydrogen or methyl;
c) $R_6$ is methyl;
d) X is oxygen;
e) X is absent and $R_6$ is hydrogen;
f) $R_7$, and $R_8$ independently of each other, are hydrogen, chloro or bromo; with the proviso that at least one of $R_7$ and $R_8$ is different from hydrogen;
g) m is 1.

In preferred compounds of formula Ia,
$R_3$ is hydrogen, methyl or ethyl; $R_4$ is hydrogen or methyl; $R_6$ is methyl; X is oxygen or X is absent and $R_6$ is hydrogen; $R_7$, and $R_8$ independently of each other, are hydrogen, chloro or bromo; with the proviso that at least one of $R_7$ and $R_8$ is different from hydrogen; and m is 1. In said preferred compounds, $R_8$ is preferably attached at the 5- or 6 position of the ring.

In said preferred compounds, $R_7$ and $R_8$ are preferably both chloro.

In preferred compounds of formula Ib,
$R_3$ is hydrogen, methyl or ethyl; $R_4$ is hydrogen or methyl; $R_6$ is methyl; X is oxygen or X is absent and $R_6$ is hydrogen; $R_7$, and $R_8$ independently of each other, are hydrogen, chloro or bromo; with the proviso that at least one of $R_7$ and $R_8$ is different from hydrogen; and m is 1. In said preferred compounds, $R_8$ is preferably attached at the 5- or 6 position of the ring.

In said preferred compounds, $R_7$ and $R_8$ are preferably both chloro.

Especially preferred compounds of formula Ia and Ib are those, wherein
$R_3$ is methyl;
$R_4$ is hydrogen;
X is absent and $R_6$ is hydrogen; or
X is oxygen and $R_6$ is methyl;
$R_7$, and $R_8$ independently of each other, are hydrogen or chloro; with the proviso that at least one of $R_7$ and $R_8$ is different from hydrogen; and
m is 1.

In said especially preferred compounds, $R_8$ is preferably attached at the 5- or 6 position of the ring.

Further preferred compounds of formula Ia are those, wherein
$R_3$ is methyl;
$R_4$ is hydrogen;

X is oxygen and $R_6$ is methyl;
$R_7$, and $R_8$ independently of each other, are hydrogen or chloro; with the proviso that at least one of $R_7$ and $R_8$ is different from hydrogen; and
m is 1.

In said preferred compounds, $R_8$ is preferably attached at the 5- or 6 position of the ring.

In said preferred compounds, $R_7$ and $R_8$ are preferably both chloro.

Further preferred compounds of formula Ia are those, wherein
$R_3$ is methyl;
$R_4$ is hydrogen;
X is oxygen and $R_6$ is methyl;
$R_7$, and $R_8$ independently of each other, are hydrogen or bromo; with the proviso that at least one of $R_7$ and $R_8$ is different from hydrogen; and
m is 1.

In said preferred compounds, $R_8$ is preferably attached at the 5- or 6 position of the ring.

Further preferred compounds of formula Ib are those, wherein
$R_3$ is methyl;
$R_4$ is hydrogen;
X is oxygen and $R_6$ is methyl;
$R_7$, and $R_8$ independently of each other, are hydrogen or chloro; with the proviso that at least one of $R_7$ and $R_8$ is different from hydrogen; and
m is 1.

In said preferred compounds, $R_8$ is preferably attached at the 5- or 6 position of the ring.

In said preferred compounds, $R_7$ and $R_8$ are preferably both chloro.

Further preferred compounds of formula Ib are those, wherein
$R_3$ is methyl;
$R_4$ is hydrogen;
X is oxygen and $R_6$ is methyl;
$R_7$, and $R_8$ independently of each other, are hydrogen or bromo; with the proviso that at least one of $R_7$ and $R_8$ is different from hydrogen; and
m is 1.

In said preferred compounds, $R_8$ is attached at the 5- or 6 position of the ring.

Especially preferred compounds of formula Ia those, wherein
$R_3$ is methyl;
$R_4$ is hydrogen;
X is absent and $R_6$ is hydrogen;
$R_7$, and $R_8$ independently of each other, are hydrogen or chloro; with the proviso that at least one of $R_7$ and $R_8$ is different from hydrogen; and
m is 1.

In said preferred compounds, $R_8$ is attached at the 5- or 6 position of the ring.

Especially preferred compounds of formula Ib are those, wherein
$R_3$ is methyl;
$R_4$ is hydrogen;
X is absent and $R_6$ is hydrogen; or
$R_7$, and $R_8$ independently of each other, are hydrogen or chloro; with the proviso that at least one of $R_7$ and $R_8$ is different from hydrogen; and
m is 1.

In said preferred compounds, $R_8$ is attached at the 5- or 6 position of the ring.

Compounds of formula Ia may be prepared according to the following general synthesis pathways:

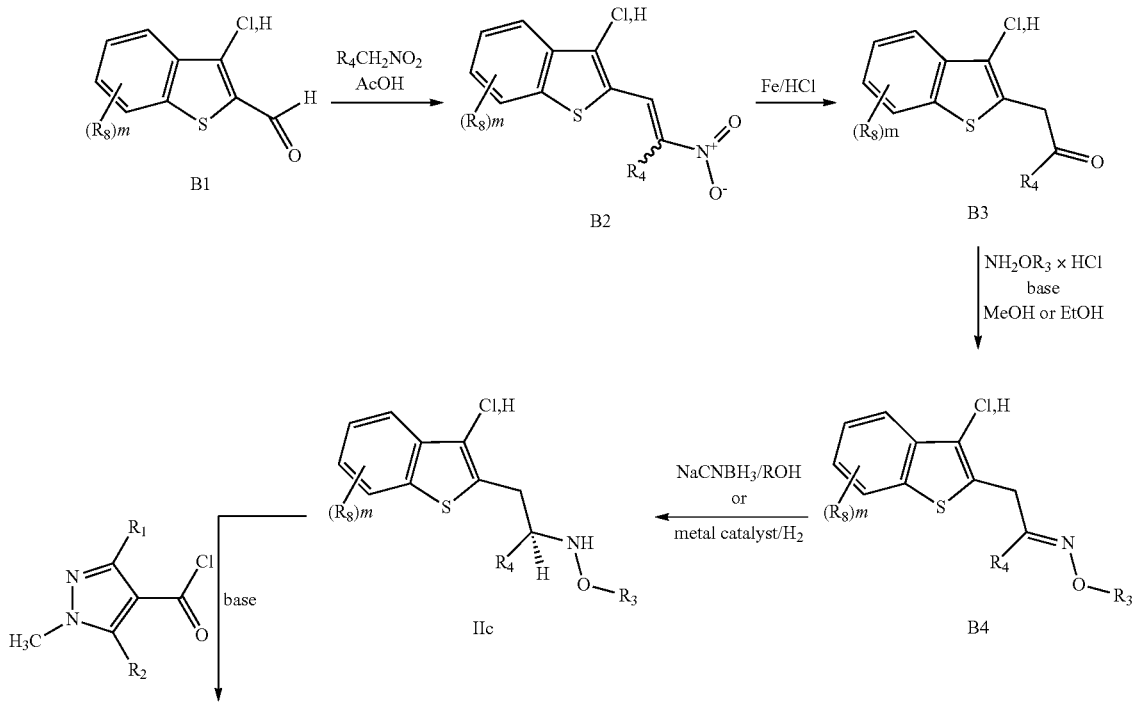

Scheme 1: In scheme 1, 2a and 2b, X is absent $R_6$ is hydrogen and $R_7$ is hydrogen or chloro.

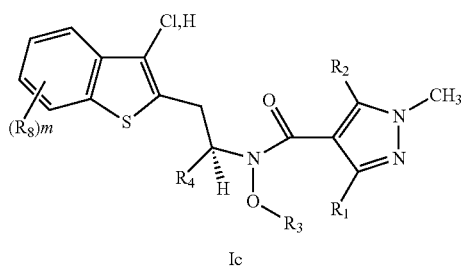

Ic

The known aldehyde intermediates B1 are transformed to the nitroolefines B2 under standard reaction conditions known to persons skilled in the art. The nitroolefines B2 are treated with Fe and HCl and deliver the ketones B3 in good yields. Further reaction with hydroxylamine or alkylated hydroxylamines and reduction with cyanoborohydride in the presence of AcOH or optionally in AcOH/alcohol mixtures gave the hydroxy respective alkoxy alkylamines. Transformation to the final amides could be performed under reaction conditions known in the art using activated heterocyclic acid derivatives (e.g. acid chlorides).

Benzthienylaldehydes B1 are transformed to the nitroolefines B2 under standard Henry conditions using nitroethane as reagent. Reaction of the nitroolefines B2 under mild conditions ($SnCl_2$/methanol, 0° C. to ambient temperature) affords the oximes B3a having the methoxy group in the linker. The transformation of the oxime B3a to the oximes B4 could be best achieved by reaction of the oximes with o-alkylated hydroxylamine hydrochlorides in the presence of a base such as pyridine or triethylamine. Reduction to the o-alkylamide is described above.

Scheme 2a:

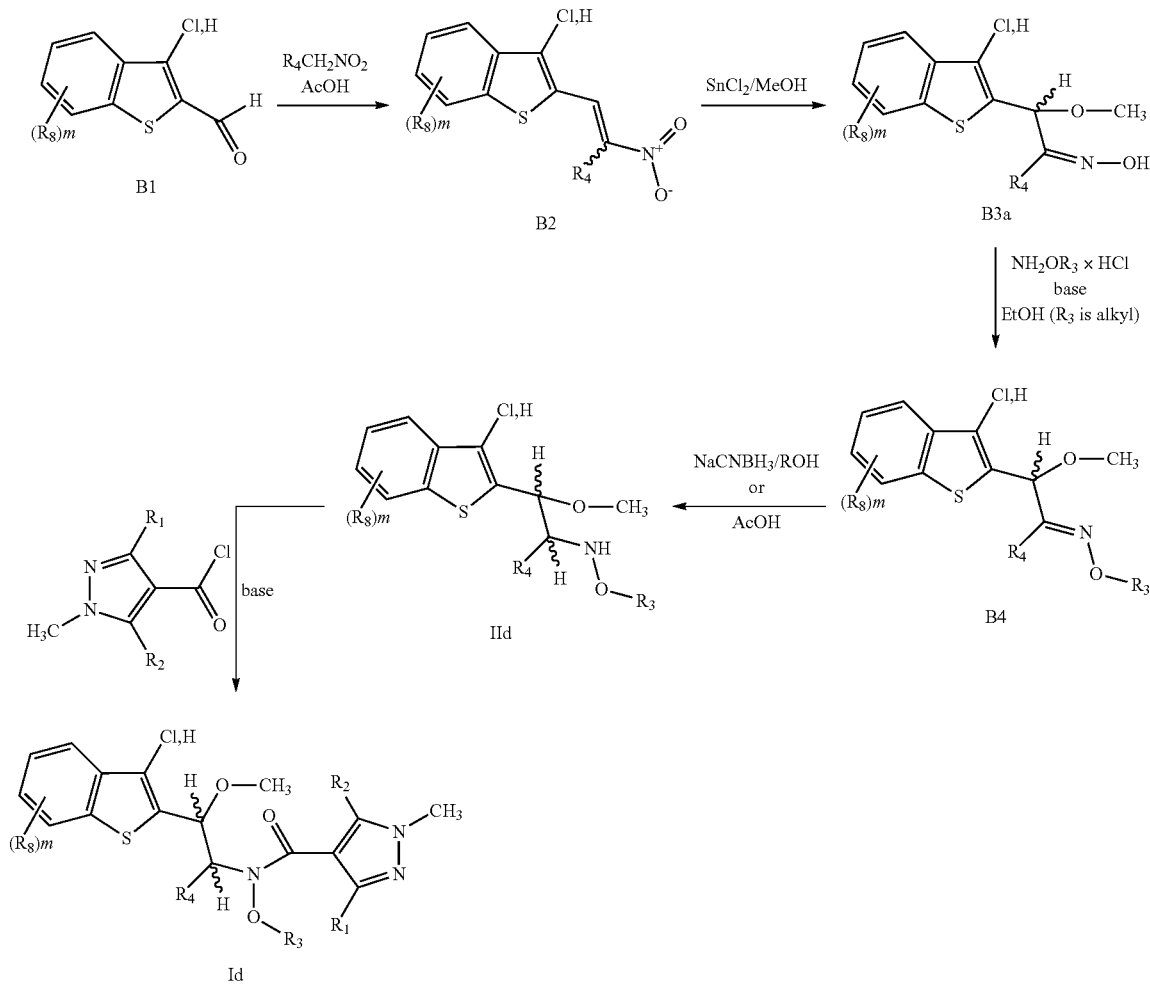

Scheme 2b:

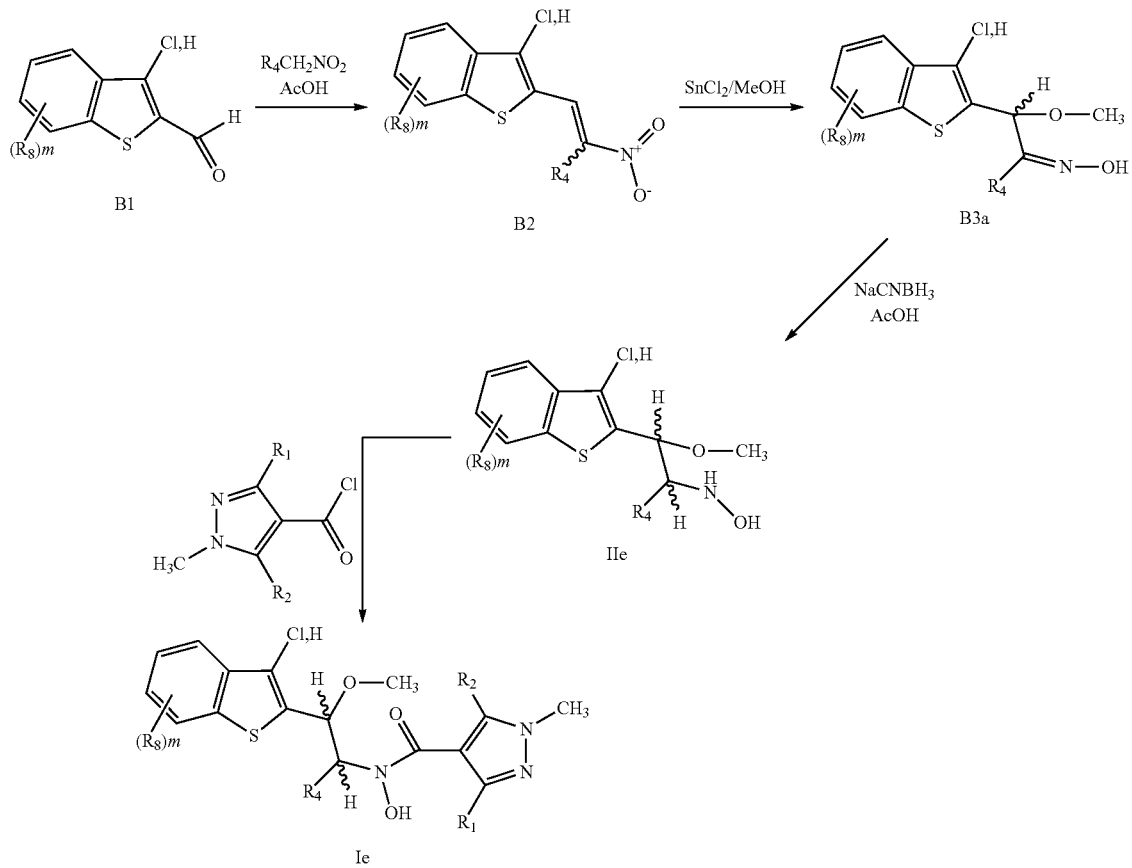

Scheme 2b illustrates a simple synthesis fo N-hydroxy amides IIe. Intermediates B3a (synthesis as described in scheme 2a) were reduced with cyanoborohydride using acetic acid as the solvent. The synthesis of compounds of formula Ie can be preferably performed by the reaction of N-hydroxyamine with the heterocyclic acid chloride without the presence of a base. The reactions illustrated in schemes 1, 2a and 2b can also be used for the preparation of the compounds of formula Ib.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo-[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The intermediates of formula II

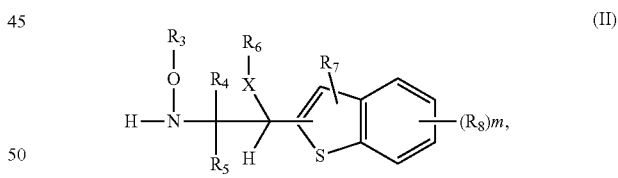

wherein $R_3$, $R_4$, $R_5$, $R_6$, $R_7$, $R_8$, m and X are as defined under formula I above, are especially developed for the preparation of the compounds of formula I and therefore constitute a further object of the present invention.

Preferred intermediates of formula II are represented by the compounds of formula IIa and IIb:

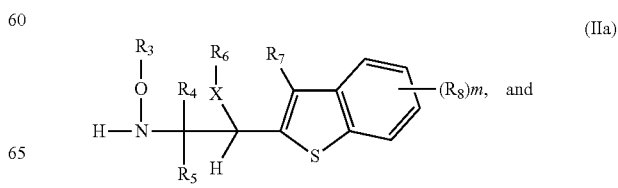

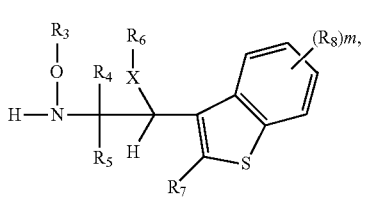

(IIb)

wherein $R_3$, $R_4$, $R_5$, $R_6$, $R_7$, $R_8$, m and X are as defined under formula I above. The preferred substituent definitions for the compounds of formula I are also valid for the compounds of formula II, IIa and IIb.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisams, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: *Fungi imperfecti* (e.g. *Botrytis, Pyricularia, Helminthosporium, Fusarium, Septoria, Cercospora* and *Alternaria*) and *Basidiomycetes* (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as acitve ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as acitve ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as acitve ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection. According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray. The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing *Zygomycosis* such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-Difluoromethyl-1-methyl-1H-pyrazole-4-carboxylic acid [2-(3,5-dichlorobenzo[b]thiophen-2-yl)-1-methyl-ethyl]methoxyamide (Compound No. 1.001)

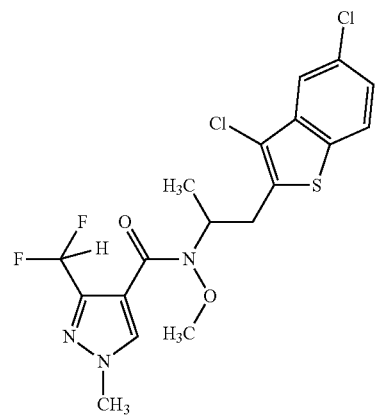

In a sulfonation flask, 0.2 g (0.69 mmol) of N-[2-(3,5-dichlorobenzo[b]thiophen-2-yl)1-methyl-1-ethyl]-O-methylhydroxylamine and 0.12 ml (0.83 mmol) triethylamine were dissolved in 7 ml of methylenechloride. Then a mixture of 0.13 mg (0.69 mmol) 3-difluoromethyl-1-methyl-1H-pyrazole-4-carboxylic acid chloride and 2 ml of methylenechloride was slowly added at ambient temperature under stirring. After stirring the mixture for 16 h at ambient temperature, the solvent was distilled off and the residue purified by column chromatography over silicagel (eluent: heptane/ethylacetate 3:2). Yield: 0.3 g (quantitative) of a white powder; m.p. 129-131° C.

a) Preparation of 1-(3,5-dichlorobenzo[b]thiophen-2-yl)propan-2-one oxime

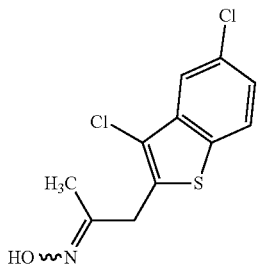

In a sulfonation flask 7 g (24.3 mmol) 3,5-dichloro-2-((E)-nitropropenyl)benzo[b]thiophene (synthesis described in WO 09/003672) was dissolved in 105 ml of methanol. Then 11 g (48.6 mmol) tindichloridedihydrate was added and the mixture stirred for 16 h at ambient temperature. For work up the mixture was diluted with 1 L of water and the pH was adjusted to 8 by addition of aqueous saturated sodiumhydrogenecarbonate solution. The resulting precipitate was dissolved in ethylacetate and the organic phase was washed twice with brine. The organic phase was dried over sodiumsulfate and the solvent distilled off in a water jet vacuum. The crude product (6.4 g oil) was purified by column chromatography over silicagel (eluent: heptane/ethylacetate 6:1). Yield: 1.25 g (18% of theory) of a white powder; m.p. 133-138° C.

b) Preparation of 1-(3,5-dichlorobenzo[b]thiophen-2-yl)propan-2-one O-methyl oxime

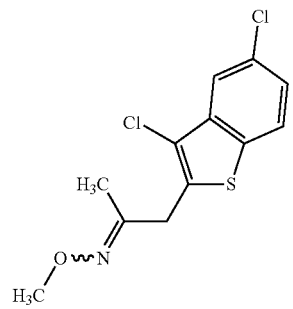

In a sulfonation flask 0.6 g (2.2 mmol) of the oxime, prepared as described before, was dissolved in 12 ml of methanol. Then 0.45 g (5.47 mmol) O-methylhydroxylamine hydrochloride and 0.44 ml (5.47 mmol) of pyridine were added to the solution and the resulting mixture stirred at ambient temperature for 24 h. After finalisation of the reaction, 120 ml of water was added. Extraction with ethylacetate, treatment of the ethylacetate phase with brine, drying the organic phase over sodium sulphate and distilling off the solvent in a water jet vacuum delivered the raw material. Purification could be achieved by column chromatography over silicagel (eluent: heptane/ethylacetate 6:1). Yield: 0.6 g (quantitative) of a white powder; m.p. 65-68° C.

c) Preparation of N-[2-(3,5-dichlorobenzo[b]thiophen-2-yl)-1-methyl-ethyl]-O-methyl-hydroxylamine (Compound 3.001)

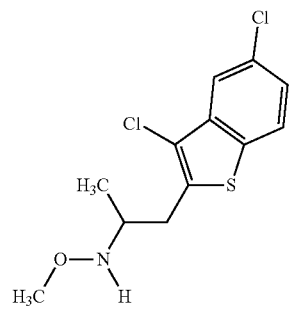

In a sulfonation flask 1 g (3.47 mmol) of the O-methyloxime described above was dissolved in 10 ml of acetic acid. After addition of 0.44 g (6.94 mmol) of sodiumcyanoborohydride the resulting mixture was stirred at ambient temperature for 16 hours. After finalisation of the reaction, the solution was carefully diluted with 100 ml of water and the pH was adjusted to 10 by addition of 4N sodiumhydroxide solution. The waterphase was extracted three times with methylenechloride and the combined organic phase was washed twice with brine. After drying over sodiumsulfate and evaporation of the solvent in a waterjet vacuum, the raw material (1 g of a yellow oil) was obtained. Purification could be achieved by using column chromatography over silicagel (eluent: heptane/ethylacetate 6:1). Yield: 0.7 g (70%) of a yellow oil (NMR-data see table 9).

Tables 1 to 3: Compounds of formula Ia:

The invention was further illustrated by the preferred individual compounds of formula (Ia) listed below in Tables 1 to. Characterising data is given in Table.

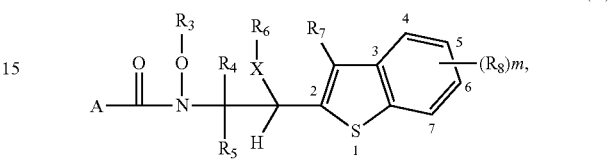

In the compounds of formula Ia, A is selected from the groups consisting of $A_1$,

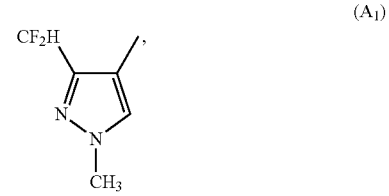

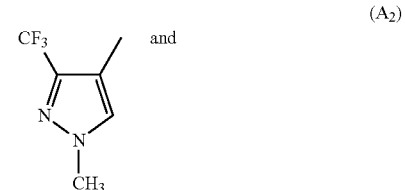

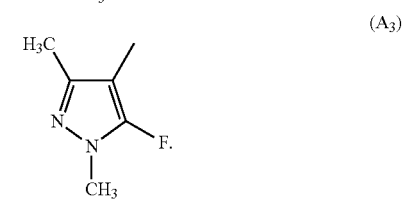

Each of Tables 1 to 3, which follow the Table Y below, comprises 35 compounds of the formula (Ia) in which $R_4$, $R_5$, $R_7$, X, $R_7$, $R_8$ and m have the values given in Table Y and A has the value given in the relevant Table 1 to 3. Thus Table 1 corresponds to Table Y when Y is 1 and A has the value given under the Table 1 heading, Table 2 corresponds to Table Y when Y is 2 and A has the value given under the Table 2 heading, and so on for Table 3.

In Tables 1 to 3 below "Me" stands for methyl, "Et" stands for ethyl and $R_5$ is hydrogen.

TABLE Y chemical designations of the substituents of the compounds of formula Ia and Ib:

| Cpd No. | $R_3$ | $R_4$ | $R_6$ | X | $R_7$ | $R_8$ |
|---|---|---|---|---|---|---|
| Y.001 | Me | Me | H | absent | Cl | 5-Cl |
| Y.002 | Me | Me | H | absent | Cl | 6-Cl |

TABLE Y-continued chemical designations of the substituents
of the compounds of formula Ia and Ib:

| Cpd No. | $R_3$ | $R_4$ | $R_6$ | X | $R_7$ | $R_8$ |
|---|---|---|---|---|---|---|
| Y.003 | Me | Me | H | absent | H | 5-Cl |
| Y.004 | Me | Me | H | absent | H | 6-Cl |
| Y.005 | Me | Me | H | absent | Cl | H |
| Y.006 | Me | Me | H | absent | Cl | 5-Br |
| Y.007 | Me | Me | H | absent | Cl | 6-Br |
| Y.008 | Me | H | H | absent | Cl | 5-Cl |
| Y.009 | Me | H | H | absent | Cl | 6-Cl |
| Y.010 | H | Me | H | absent | Cl | 5-Cl |
| Y.011 | H | Me | H | absent | Cl | 6-Cl |
| Y.012 | i-Pr | Me | H | absent | Cl | 5-Cl |
| Y.013 | i-Pr | Me | H | absent | Cl | 6-Cl |
| Y.014 | Me | Me | Me | O | Cl | 5-Cl |
| Y.015 | Me | Me | Me | O | Cl | 6-Cl |
| Y.016 | Me | Me | Me | O | Cl | 5-Br |
| Y.017 | Me | Me | Me | O | Cl | 6-Br |
| Y.018 | Me | Me | Me | O | Cl | H |
| Y.019 | Me | Me | Me | O | H | 5-Cl |
| Y.020 | Me | Me | Me | O | H | 6-Cl |
| Y.021 | Me | Me | Me | O | H | 5-Br |
| Y.022 | Me | H | Me | O | Cl | 5-Cl |
| Y.023 | Me | H | Me | O | Cl | 6-Cl |
| Y.024 | H | Me | Me | O | Cl | 5-Cl |
| Y.025 | H | Me | Me | O | Cl | 6-Cl |
| Y.026 | i-Pr | Me | Me | O | Cl | 5-Cl |
| Y.027 | i-Pr | Me | Me | O | Cl | 6-Cl |
| Y.028 | Me | Me | Me | absent | Cl | 5-Cl |
| Y.029 | Me | Me | Me | absent | Cl | 6-Cl |
| Y.030 | Me | Me | Me | O | Cl | 5-Cl |
| Y.031 | Me | Me | Me | O | Cl | 6-Cl |
| Y.032 | Me | H | Me | O | Cl | 5-Cl |
| Y.033 | H | Me | H | absent | Cl | 5-Br |
| Y.034 | H | Me | H | absent | Cl | 6-Br |

Table 1 provides 34 compounds of formula (Ia), wherein A is $A_1$

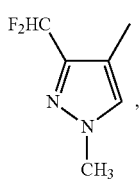
(A₁)

and $R_3$, $R_4$, $R_6$, X, $R_7$ and $R_8$ are as defined in Table Y.

For example, compound 1.001 has the following structure:

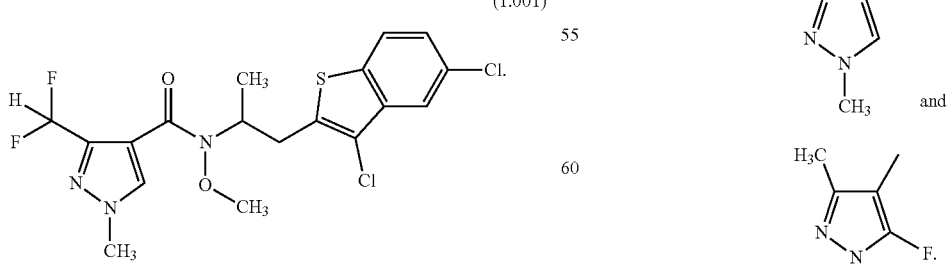
(1.001)

Table 2 provides 34 compounds of formula (Ia), wherein A is $A_2$

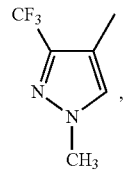
(A₂)

and $R_3$, $R_4$, $R_6$, X, $R_7$ and $R_8$ are as defined in Table Y.

Table 3 provides 34 compounds of formula (Ia), wherein A is $A_3$

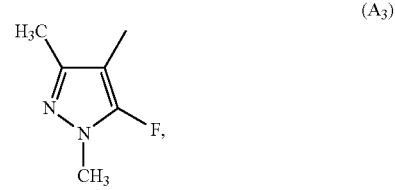
(A₃)

and $R_3$, $R_4$, $R_6$, X, $R_7$ and $R_8$ are as defined in Table Y.

Tables 4 to 6: Compounds of formula Ib:

The invention was further illustrated by the preferred individual compounds of formula (Ia) listed below in Tables 4 to 6. Characterising data are given in Table 9.

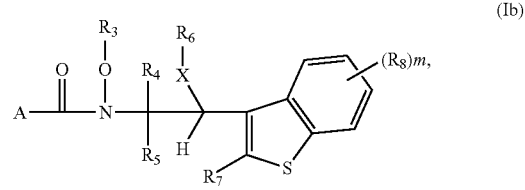
(Ib)

In the compounds of formula Ib, A is selected from the groups consisting of $A_1$,

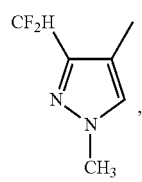
(A₁)

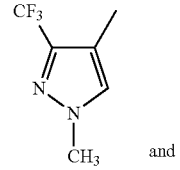
(A₂)

and

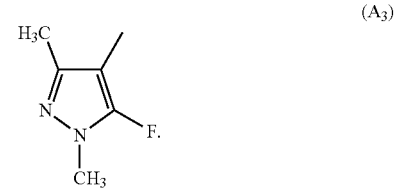
(A₃)

Each of Tables 4 to 6, which follow the Table Y below, comprises 34 compounds of the formula (Ib) in which $R_4$, $R_5$, $R_7$, X, $R_7$, and $R_8$ have the values given in Table Y and A has the value given in the relevant Table 4 to 6. Thus Table 4 corresponds to Table Y when Y is 4 and A has the value given under the Table 4 heading, Table 5 corresponds to Table Y when Y is 5 and A has the value given under the Table 5 heading, and so on for Table 6.

Table 4 provides 34 compounds of formula (Ib), wherein A is $A_1$

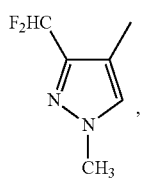

(A₁)

and $R_3$, $R_4$, $R_6$, X, $R_7$ and $R_8$ are as defined in Table Y.

Table 5 provides 34 compounds of formula (Ib), wherein A is $A_2$

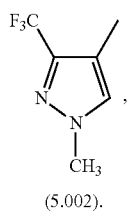

(A₂)

(5.002).

and $R_3$, $R_4$, $R_6$, X, $R_7$ and $R_8$ are as defined in Table Y.

Table 6 provides 34 compounds of formula (Ib), wherein A is $A_3$

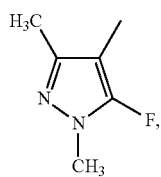

(A₃)

and $R_3$, $R_4$, $R_6$, X, $R_7$ $R_8$ and $R_9$ are as defined in Table Y.

Tables 7-8: chemical designations of the substituents of the compounds of formula IIa and IIb (amine intermediates):

| Cpd No. | $R_3$ | $R_4$ | $R_6$ | X | $R_7$ | $R_8$ |
|---|---|---|---|---|---|---|
| Z.001 | Me | Me | H | absent | Cl | 5-Cl |
| Z.002 | Me | Me | H | absent | Cl | 6-Cl |
| Z.003 | Me | Me | H | absent | Cl | 5-Br |
| Z.004 | Me | Me | H | absent | Cl | 6-Br |
| Z.005 | Me | Me | H | absent | Cl | H |
| Z.006 | Me | Me | H | absent | H | 5-Cl |
| Z.007 | Me | Me | H | absent | H | 6-Cl |
| Z.008 | Me | H | H | absent | Cl | 5-Cl |
| Z.009 | Me | H | H | absent | Cl | 6-Cl |
| Z.010 | H | Me | H | absent | Cl | 5-Cl |
| Z.011 | H | Me | H | absent | Cl | 6-Cl |

-continued

| Cpd No. | $R_3$ | $R_4$ | $R_6$ | X | $R_7$ | $R_8$ |
|---|---|---|---|---|---|---|
| Z.012 | i-Pr | Me | H | absent | Cl | 5-Cl |
| Z.013 | i-Pr | Me | H | absent | Cl | 6-Cl |
| Z.014 | Me | Me | Me | O | Cl | 5-Cl |
| Z.015 | Me | Me | Me | O | Cl | 6-Cl |
| Z.016 | Me | Me | Me | O | Cl | 5-Br |
| Z.017 | Me | Me | Me | O | Cl | 6-Br |
| Z.018 | Me | Me | Me | O | Cl | H |
| Z.019 | Me | Me | Me | O | H | 5-Cl |
| Z.020 | Me | Me | Me | O | H | 6-Cl |
| Z.021 | Me | Me | Me | O | H | 5-Br |
| Z.022 | Me | Me | Me | O | H | 6-Br |
| Z.023 | Me | H | Me | O | Cl | 5-Cl |
| Z.024 | Me | H | Me | O | Cl | 6-Cl |
| Z.025 | H | Me | Me | O | Cl | 5-Cl |
| Z.026 | H | Me | Me | O | Cl | 6-Cl |
| Z.027 | i-Pr | Me | Me | O | Cl | 5-Cl |
| Z.028 | i-Pr | Me | Me | O | Cl | 6-Cl |

Table 7 (Z=7) describes 28 compounds (amine intermediates) of formula (IIa)—physical data are given in Table 9:

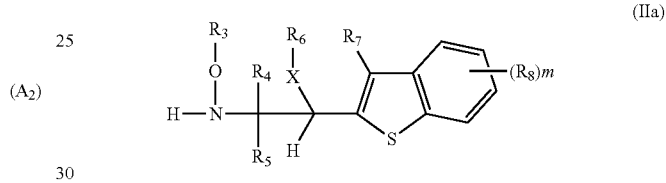

(IIa)

Table 8 (Z=8) describes 28 compounds (amine intermediates) of formula (IIb)—physical data are given in Table 9:

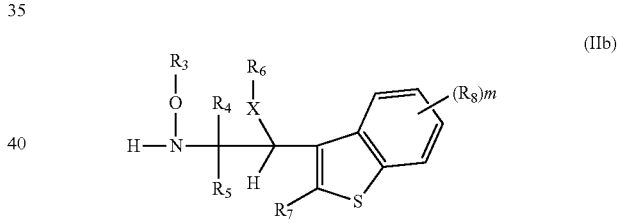

(IIb)

Table 9: Characterising Data:

Table 9 shows selected melting point and selected NMR data for compounds of Tables 1 to 8. $CDCl_3$ is used as the solvent for NMR measurements, unless otherwise stated. If a mixture of solvents is present, this is indicated as, for example: $CDCl_3/d_6$-DMSO). No attempt is made to list all characterising data in all cases.

In Table 9 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

TABLE 9

| Cpd No. | 1H-NMR data: (ppm/multiplicity/ number of Hs) | MS [M + H]+ | m.p. (° C.) | LCMS data |
|---|---|---|---|---|
| 1.001 | | | 129-131 | |
| 1.002 | | | 148-149 | |
| 1.006 | | | 164-166 | |
| 1.010 | | | 196-197 | |
| 1.014 | | | 176-177 | |
| 1.015 | | | 123-126 | |
| 1.016 | | | 163-164 | |
| 1.024 | | | 190-192 | |
| 1.033 | | | 204-206 | |
| 2.001 | 1.43/d/3H, 3.24/m/1H, 3.39/m/1H, 3.63/s/3H, 3.89/m/3H, 4.71/m/1H, 7.35/dd/1H, 7.68/d/1H, 7.75/dd/1H | 466/468 | | Positive IEMS |
| 2.002 | | 466/468 | | Positive IEMS |
| 2.014 | | | 128-130 | |
| 2.015 | | | 136-138 | |
| 2.024 | | | 170-173 | |
| 3.001 | 1.47/d/3H, 2.01/s/3H, 3.19/m/1H, 3.36/m/1H, 3.65/s/3H, 3.70/s/3H, 4.65/m/1H, 7.32/dd/1H, 7.65/d/1H, 7.71/d/1H | 430/432 | | Positive IEMS |
| 3.002 | | 430/432 | | Positive IEMS |

Formulation examples for compounds of formula I:

Example F-1.1 to F-1.2

Emulsifiable Concentrates

| Components | F-1.1 | F-1.2 |
|---|---|---|
| compound of Tables 1-6 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1-6 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1-6 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1-6 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1-6 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1-6 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |

-continued

| Components | F-6.1 | F-6.2 | F-6.3 |
|---|---|---|---|
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1-6 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Example

Example B-1

Action Against *Fusarium culmorum* (Head Blight/Spikelet)

Wheat spikelets are placed on agar in multiwell plates (24-well format) and sprayed with test solutions (60 ppm active ingredient). After drying, the spikelets are inoculated with a spore suspension of the fungus. After appropriate incubation the activity of a compound is assessed 6 dpi (days after inoculation) as preventative fungicidal activity. Compounds 1.001, 1.002, 1.006, 1.015 and 2.002 show very good activity in this test (≧80% inhibition).

Example B-2

Action Against *Fusarium graminearum*, Syn. *Gibberella zeae*, (Head Blight/Spikelet)

Wheat spikelets are placed on agar in multiwell plates (24-well format) and sprayed with test solutions (60 ppm active ingredient). After drying, the spikelets are inoculated with a spore suspension of the fungus. After appropriate incubation the activity of a compound is assessed 6 dpi (days after inoculation) as preventative fungicidal activity. Compounds 1.001, 1.002, 1.006, 1.015 and 2.015 show very good activity in this test (≧80% inhibition).

Example B-3

Action Against *Pyrenophora teres* (Net Blotch)

Barley leaf segments are placed on agar in multiwell plates (24-well format) and sprayed with test solutions (60 ppm active ingredient). After drying, the leaf disks are inoculated with a spore suspension of the fungus. After appropriate incubation the activity of a compound is assessed 4 dpi (days after inoculation) as preventive fungicidal activity. Compounds 1.001, 1.006, 1.002, 1.010, 1.015, 1.016, 1.033, 2002, 2.015 and 3.002 show very good activity in this test (≧80% inhibition).

Example B-4

Action Against *Erysiphe graminis* f. sp. *hordei* (Barley Powdery Mildew)

Barley leaf segments are placed on agar in multiwell plates (24-well format). The leaf disks are inoculated with spores of the fungus. After 24 h the leaf disk sprayed with test solutions (60 ppm active ingredient). After appropriate incubation the activity of a compound is assessed 7 dpi (days after inoculation) as curativ fungicidal activity. Compounds 1.002, 1.006, 1.015, 1.016, 2.002, 2.015 and 3.002 show very good activity in this test (≧80%) inhibition).

Example B-5

Action Against *Puccinia recondita* I Wheat/Leaf Disc Preventative (Brown Rust)

Wheat leaf segments are placed on agar in multiwell plates (24-well format) and sprayed with test solutions (60 ppm active ingredient). After drying, the leaf disks are inoculated with a spore suspension of the fungus. After appropriate incubation the activity of a compound is assessed 8 dpi (days after inoculation) as preventive fungicidal activity. Compounds 1.002, 1.006, 1.015, 1.016, 2.002 and 3.002 show very good activity in this test (≧80% inhibition).

Example B-6

Action Against *Puccinia recondita*/Wheat/Leaf Disc Curative (Brown Rust)

Wheat leaf segments are placed on agar in multiwell plates (24-well format). The leaf disks are then inoculated with a spore suspension of the fungus. One day after inoculation the test solution is applied (200 ppm active ingredient). After appropriate incubation the activity of a compound is assessed 8 dpi (days after inoculation) as curative fungicidal activity. Compound 1.006 shows very good activity in this test (80% inhibition).

Example B-7

Action Against *Phaeosphaeria nodorum* (*Septoria nodorum*)/Wheat/Leaf Disc Preventative (Glume Blotch)

Wheat leaf segments are placed on agar in a multiwell plate (24-well format) and sprayed with test solutions (60 ppm active ingredient). After drying, the leaf disks are inoculated with a spore suspension of the fungus. After appropriate incubation the activity of a compound is assessed 4 dpi (days after inoculation) as preventive fungicidal activity. Compound 1.002, 1.006, 1.015, 2.002 and 3.002 shows very good activity in this test (80% inhibition).

Example B-8

Action Against *Botryotinia fuckeliana* (*Botrytis cinerea*)/Liquid Culture (Gray Mould)

Conidia of the fungus from cryogenic storage are directly mixed into nutrient broth. After placing a (DMSO) solution (200 ppm active ingredient) of the test compounds into a microtiter plate (96-well format) the nutrient broth containing the fungal spores is added. The test plates are incubated at 24° C. and the inhibition of growth is determined photometrically after 3-4 days. Compounds 1.002, 1.006, 1.015, 1.016, 1.033, 2.002, 2.015 and 3.002 show very good activity in this test ($\geq$80% inhibition).

Example B-9

Action Against *Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of the test compounds (200 ppm active ingredient) into a microtiter plate (96-well format) the nutrient broth containing the fungal spores is added. The test plates are incubated at 24° C. and the inhibition of growth is measured photometrically after 6-7 days. Compounds 1.002, 1.006, 1.010, 1.015, 1.016, 1.033, 2.002, 2.015 and 3.002 show very good activity in this test (80% inhibition).

Example B-10

Action Against *Mycosphaerella graminicola* (*Septoria tritici*)/Liquid Culture (*Septoria* Blotch)

Conidia of the fungus from cryogenic storage are directly mixed into nutrient broth (PDB potato dextrose broth). After placing a (DMSO) solution of the test compounds (200 ppm active ingredient) into a microtiter plate (96-well format) the nutrient broth containing the fungal spores is added. The test plates are incubated at 24° C. and the inhibition of growth is measured photometrically after 4 days. Compounds 1.002, 1.006, 1.010, 1.015, 1.016, 1.033, 2.002, 2.015 and 3.002 show very good activity in this test (80% inhibition).

Example B-11

Action Against *Monographella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of the test compounds (200 ppm active ingredient) into a microtiter plate (96-well format) the nutrient broth containing the fungal spores is added. The test plates are incubated at 24° C. and the inhibition of growth is measured photometrically after 4-6 days. Compounds 1.002, 1.006, 1.010, 1.015, 1.016, 2.002 and 2.015 show very good activity in this test (80% inhibition).

What is claimed is:

1. A compound of formula I

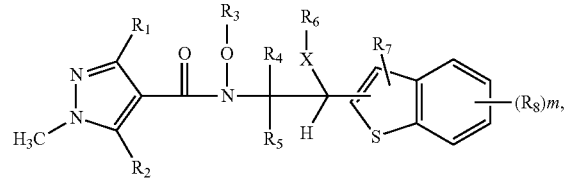

(I)

wherein
$R_1$ is $C_1$-$C_4$alkyl or $C_1$-$C_4$haloalkyl;
$R_2$ is hydrogen, fluoro or chloro;
$R_3$ is hydrogen or $C_1$-$C_4$alkyl;
$R_4$ and $R_5$, independently from each other, are hydrogen or $C_1$-$C_4$alkyl;
X is oxygen, sulfur or absent;
$R_6$ is $C_1$-$C_4$alkyl or $C_1$-$C_4$haloalkyl if X is oxygen or sulfur, or is hydrogen if X is absent;
$R_7$ and $R_8$ independently from each other, are hydrogen, halogen or =$R_9$; with the proviso that at least one of $R_7$ and $R_8$ is different from hydrogen;
m is 1, 2, 3 or 4;
$R_9$ is hydrogen, $C_1$-$C_6$alkyl, $C_1$-$C_6$haloalkyl or $C_1$-$C_4$alkoxyalkyl;
and agrochemically acceptable salts/stereoisomers/diastereoisomers/enantio-mers/tautomers and N-oxides thereof.

2. A compound according to claim 1, wherein
$R_1$ is difluoromethyl, trifluoromethyl or methyl;
$R_2$ is hydrogen or fluoro;
$R_3$ is hydrogen, methyl or ethyl;
$R_4$ is hydrogen or methyl;
$R_5$ is hydrogen or methyl;
$R_6$ is methyl; and X is oxygen;
or X is absent and $R_6$ is hydrogen;
$R_7$, and $R_8$ independently of each other, are hydrogen, chloro or bromo; with the proviso that at least one of $R_7$ and $R_8$ is different from hydrogen.

3. A compound according to claim 2, wherein X is absent and $R_6$ is hydrogen.

4. A compound of formula I according to claim 1 represented by the compounds of formula Ia:

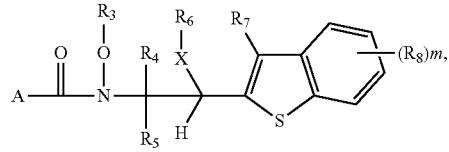

(Ia)

wherein A is selected from the groups consisting of $A_1$, $A_2$, and $A_3$

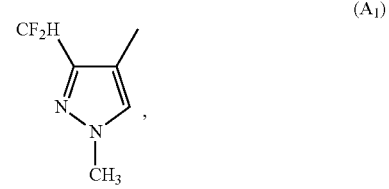

($A_1$)

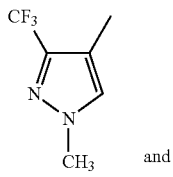
(A₂) and

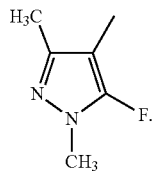
(A₃)

and R₃, R₄, R₆, R₇, R₈, m and X are as defined under formula I in claim 1 and R₅ is hydrogen.

5. A method of controlling infestation of useful plants by phytopathogenic microorganisms, wherein a compound of formula I according to claim 1 or a composition, comprising this compound as active ingredient, is applied to the plants, to parts thereof or the locus thereof.

6. A composition for controlling and protecting against phytopathogenic microorganisms, comprising a compound of formula I according to claim 1 and an inert carrier.

* * * * *